United States Patent

Dalen et al.

[11] Patent Number: 5,183,056
[45] Date of Patent: Feb. 2, 1993

[54] INDUCTIVE MOTION SENSOR

[75] Inventors: Bjoern Dalen, Stockholm; Kenth-Ake-Sune Nilsson, Akersberga; Kurt Hoegnelid; Liliane Wecke, both of Sundbyberg, all of Sweden

[73] Assignee: Siemens Aktiengesellschaft, Munich, Fed. Rep. of Germany

[21] Appl. No.: 599,412

[22] Filed: Oct. 18, 1990

[30] Foreign Application Priority Data

Oct. 20, 1989 [EP] European Pat. Off. ........... 89119524

[51] Int. Cl.⁵ .............................................. A61B 5/103
[52] U.S. Cl. ...................................... 128/782; 73/652; 340/429; 340/689
[58] Field of Search ................... 128/774, 782; 73/652; 340/429, 689

[56] References Cited

U.S. PATENT DOCUMENTS

| | | | |
|---|---|---|---|
| 3,911,899 | 10/1975 | Hattes | 128/782 |
| 4,517,514 | 5/1985 | Howell | 73/652 |
| 4,656,458 | 4/1987 | Iwata | 340/429 |
| 4,846,195 | 6/1989 | Alt | 128/782 |
| 4,869,251 | 9/1989 | Lakholm et al. | 128/419 PG |
| 4,901,569 | 2/1990 | Lui | 340/429 |
| 5,010,893 | 4/1991 | Sholder | 128/782 |

FOREIGN PATENT DOCUMENTS

0254945A1  7/1987  European Pat. Off. .
0800935    1/1981  U.S.S.R. .................... 73/652

Primary Examiner—Max Hindenburg
Attorney, Agent, or Firm—Hill, Van Santen, Steadman & Simpson

[57] ABSTRACT

An inductive motion sensor (MS) connectable to a subject (16), the motion sensor having a coil (4) and a magnet member (3) movable relative to the coil (4). The magnet member (3) has at least four magnetic poles, whereby the number of south poles (S) is equal to the number of north poles (N). The pole strength of the magnetic poles is dimensioned and the magnetic poles are located on the magnet member (3) such that the magnet member (3) is situated in a neutral equilibrium position in a uniform magnetic field with respect to the forces exerted on the magnetic poles by the magnetic field.

13 Claims, 4 Drawing Sheets

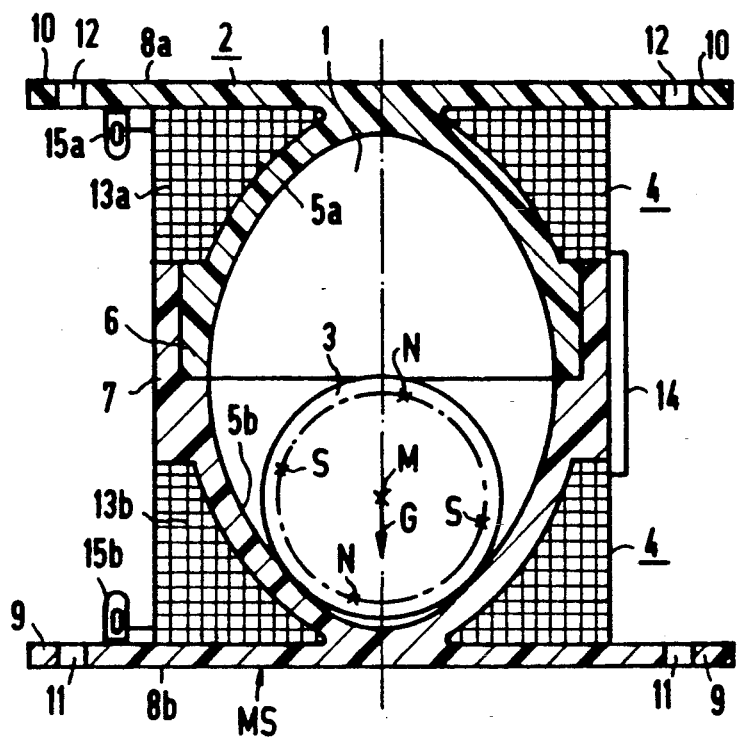
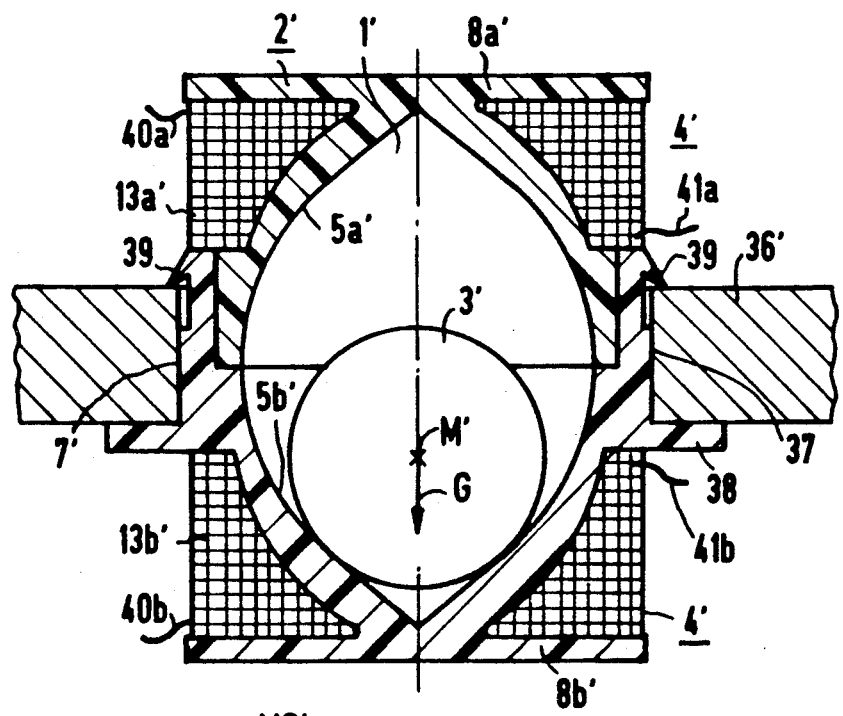

INDUCTIVE MOTION SENSOR

BACKGROUND OF THE INVENTION

The present invention is directed to an inductive motion sensor that can be attached to a subject, the inductive motion sensor having a coil and a magnet member movable relative to the coil.

The function of such motion sensors is based on the fact that dislocations of the magnet member relative to the coil occur as a result of motions of the subject to which the motion sensor is attached, thereby inducing an electrical voltage in the coil. When the motion sensor is attached to a life form in order to monitor its physical activity, the induced current is interpreted in terms of its amplitude and/or chronological change in order to be able to draw conclusions regarding the degree and/or nature of the physical activity of the life form. When, by contrast, the motion sensor is used as an anti-theft sensor, then it is generally adequate to detect the mere occurrence of an induced voltage in order to be able to determine that the article to be protected is being removed from its location.

In known motion sensors of the type initially set forth, the problem arises that due to their high sensitivity, i.e. their response to extremely small motions, disturbances occur as a result of the magnetic field of the earth or as a result of low-frequency magnetic fields emanating from electrical devices, for example electric motors. Erroneous detections often occur particularly given the occurrence of low-frequency magnetic fields, i.e. motions of the magnet member relative to the coil occur without a motion of the subject to be monitored being present.

SUMMARY OF THE INVENTION

An object of the present invention is to provide a motion sensor of the type initially cited in which disturbances due to the magnetic field of the earth and/or due to the occurrence of low-frequency magnetic fields are reliably avoided.

This object is inventively achieved in that the magnet member has at least four magnetic poles, whereby the number of south poles is equal to the number of north poles; and in that the pole strength of the magnetic poles and the location of the magnetic poles relative to the magnet member are such that the magnet member is situated in a neutral equilibrium position in a uniform magnetic field with respect to the forces exerted by the magnetic field on the magnetic poles. Since the magnetic field of the earth, just as the low-frequency magnetic fields emanating from electrical devices (it is assumed in the latter case that the motion sensor is not situated in the immediate proximity of the electrical device) are uniform magnetic fields, they do not cause any motions of the magnet member relative to the coil. Disturbances due to the magnetic fields are thus impossible. The required mobility of the magnet member relative to the coil can be achieved, for example, in that it is suspended by a thread or by one or more strings in the fashion of a pendulum.

An especially expedient embodiment of the present invention provides that the motion sensor comprises a housing surrounding a cavity, whereby the magnet member is contained in the cavity with the coil surrounding the housing. Improved manipulation of the sensor is thereby achieved, and can be further improved when the coil is wound on the outside of the housing which is then expediently fashioned as a winding member. The magnet member can be manufactured in a technologically simple manner when the magnetic poles each have the respectively same pole strength and are arranged at identical angular spacings from one another on a circular line such that a north pole is respectively followed by a south pole. In an especially simple modification of the present invention the magnet member is spherically fashioned. As a result the spherical magnet member rolls off on the wall of the cavity, and the required mobility of the magnet member relative to the coil is technologically realized in an especially simple structure. It is expedient in this context to fashion the cavity rotationally symmetrical. The advantage that the sensor works completely attitudinally independent is achieved for a spherical cavity.

When, by contrast, an attitudinally dependent function of the motion sensor is desired, the cavity can be shaped such that a roll-off of the magnet member on the wall of the cavity is made more difficult for at least one alignment of the motion sensor relative to the direction of the force of gravity. The cavity can thereby be fashioned such that the roll-off of the magnet member is more difficult or is even completely impossible. When the subject provided with such a motion sensor assumes such a position that a roll-off of the magnet member on the wall of the cavity is made more difficult or is completely impossible, the motion sensor has a reduced sensitivity or a sensitivity of zero, respectively. Only when the position of the subject changes to such an extent that an undisturbed roll-off of the magnet member on the wall of the cavity is again possible has the motion sensor been re-activated.

Particularly for applications wherein it is critical to provide a motion sensor that is dependent on attitude, it is provided in a modification of the present invention that the motion sensor comprises a housing that surrounds a cavity, whereby the magnet member is contained in the cavity and the housing is surrounded by the coil; that the magnet member is spherically fashioned and rolls off on the wall of the cavity; and that the cavity is shaped such that a roll-off of the magnet member on the wall of the preferably rotationally symmetrical cavity is at least made more difficult for at least one alignment of the motion sensor relative to the direction of the force of gravity.

The cavity can thereby be fashioned such that the roll-off of the magnet member is made more difficult or is even completely impossible. In this case, too, there is at least one alignment of the motion sensor in which a roll-off of the magnet member on the wall of the cavity is made more difficult or is completely impossible, so that the motion sensor has a reduced sensitivity or a sensitivity of zero, respectively, for this alignment. The attitudinally dependent function of the motion sensor can be realized in a simple way when the cavity has at least approximately the shape of an ellipsoid of revolution or when it is fashioned lemon-shaped.

The motion sensor of the present invention can be advantageously used as a motion sensor in a heart pacemaker whose stimulation frequency is controlled as a function of the physical activity of the patient wearing the heart pacemaker since, in contrast to inductive motion sensors previously used for this purpose, it is not attenuated by the magnetic field of the earth, so that even slight motions as occur, in particular, in conjunction with the physical activity of older patients can be sensed. It is of quite advantageous significance when a motion sensor is used in a heart pacemaker, this motion sensor working attitudinally dependent such that a roll-off of the ball on the wall of the cavity is made more difficult or is completely impossible both when the patient lies on his stomach as well as when he lies on his back. In this case, a physiologically unsubstantiated increase in the stimulation frequency for a patient at rest, particularly asleep, is impossible since the motion sensor is only sensitive again when the patient stands up or at least assumes a sitting position. By contrast to known piezoelectric motion sensors (there is a risk of a physiologically unsubstantiated increase in the stimulation frequency as a consequence of body weight pressing on the sensor when the patient lies down), physiologically unsubstantiated increases in the stimulation frequency are largely suppressed in the motion sensor of the present invention.

Another preferred employment of the motion sensor of the present invention is as a motion sensor for monitoring a bed-ridden patient, particularly in intensive care. Here, too, the advantage arises that even the slightest motions can be detected with the motion sensor of the present invention.

A further alternative preferred use of the motion sensor is as a anti-theft sensor. By contrast to known sensors that can be disabled by a strong permanent magnet, the motion sensor of the present invention cannot be disabled since the magnet member assumes a neutral equilibrium position in the magnetic field of the permanent magnet. Only extremely strong permanent magnets that are brought into the immediate proximity of the motion sensor of the present invention are capable of seriously disturbing its operation.

BRIEF DESCRIPTION OF THE DRAWINGS

The features of the present invention which are believed to be novel, are set forth with particularity in the appended claims. The invention, together with further objects and advantages, may best be understood by reference to the following description taken in conjunction with the accompanying drawings, in the several Figures in which like reference numerals identify like elements, and in which:

FIG. 6 is a cross-sectional view of a special operating condition of the motion sensor of FIGS. 1 and 2;

FIG. 9 is a cross-sectional view of a further motion sensor of the present invention.

DESCRIPTION OF THE PREFERRED EMBODIMENT

Figure 1:
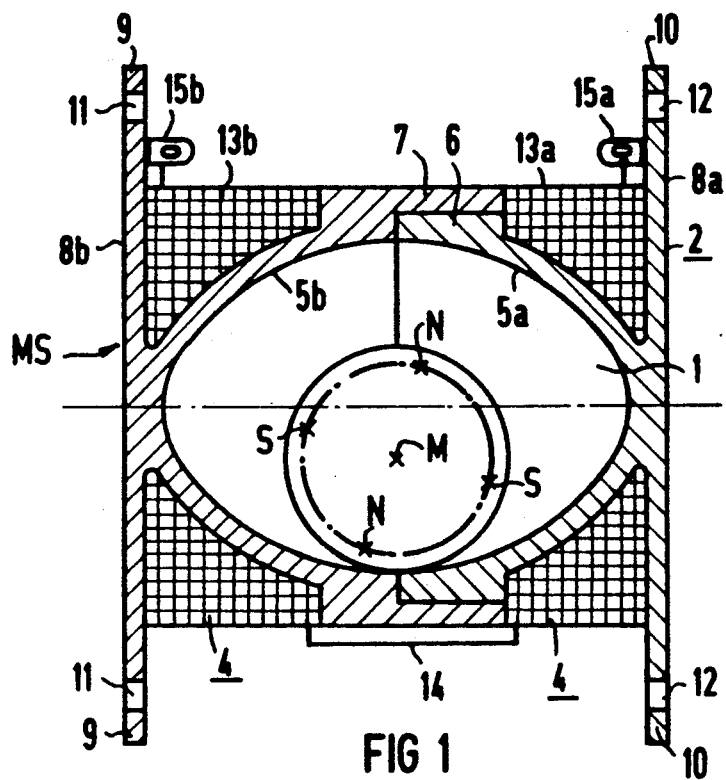
FIG. 1 is a cross-sectional view of a motion sensor of the present invention.

As shown in FIG. 1, the motion sensor MS of the present invention comprises a housing 2 that surrounds a cavity 1, a magnet member 3 situated inside the cavity 1, and a coil 4 attached to the outside of the housing 2. At motions of the motion sensor MS or, respectively, of a subject to which it is attached, the magnet member 3 rolls off on the wall of the cavity 1. Dislocations of the magnet member 3 relative to the coil 4 occur and as a result an electrical voltage is induced in the latter, indicating the occurrence of a motion.

The housing 2 is composed of two housing parts 5a and 5b that are joined to one another in a suitable way, for example by gluing, and together limit the cavity 1 that has the shape of an ellipsoid of revolution. The region of the seam present between the two housing parts 5a, 5b and adjoining the cavity 1 lies in a plane that is orientated at a right angle relative to the rotational axis (shown with a broken line) of the ellipsoid of revolution, namely at that location at which the ellipsoid of revolution has its largest diameter. As a result the housing parts 5a, 5b do not have any undercuts in the region of their walls limiting the cavity 1, so that the housing parts 5a, 5b can be simply manufactured as injection molded parts or as pressure diecast parts.

At its end facing toward the housing part 5b, the housing part 5a is provided with a centering projection 6 that has a cylindrical, outer generated surface whose center axis corresponds to the rotational axis of the ellipsoid of revolution. At its end facing toward the housing part 5a, the housing part 5b is provided with a centering edge 7 that accepts the centering projection 6 of the housing part 5a and that has a cylindrical inside wall having a diameter that corresponds to the outer generated surface diameter of the centering projection 6. The center axis of the inside wall of the centering edge 7 likewise corresponds to the rotational axis of the ellipsoid of revolution. The two housing parts 5a, 5b are thus centered relative to one another with the centering projection 6 and with the centering edge 7 such that the wall of the housing 2 limiting the cavity 1 has no offset in the region of the seam between the housing parts 5a, 5b, thereby guaranteeing a smooth roll-off of the magnet member 3.

Not considering the centering projection 6 or, respectively, the centering edge 7, the housing parts 5a, 5b have an essentially constant wall thickness, so that the outer shape of the housing 1 essentially corresponds to the shape of an ellipsoid of revolution. The housing parts 5a, 5b are each respectively provided with a flange 8a, 8b having the shape of a circular disc in the region of the points of the ellipsoid of revolution. The flanges 8a, 8b each respectively have two approximately rectangular projections 9, 10 that are provided with oblong holes 11, 12. The flanges 8a, 8b also each respectively have an outside diameter that approximately corresponds to the outside diameter of the centering edge 7.

The outside wall of the housing part 5a, the flange 8a and the centering projection 6 as well as the centering edge 7 as well as the outside wall of the housing part 5b, the flange 8b and the centering edge 7, form two channels into which a coil 4 composed of two coil sections 13a, 13b is wound. The coil 4 is composed of lacquered copper wire having a diameter in the range of 6 to 100 μm and, depending on the diameter of the lacquered copper wire, has 100 to 100,000 turns. The two coil sections 13a, 13b are connected at their ends with an electrical line 14 such that a current flowing through the coil 4 has an opposite rotational sense in both coil sections 13a, 13b. The other ends of the coil sections 13a, 13b are connected and soldered to schematically indicated solder points 15a, 15b attached to the flanges 8a, 8b. Lines can be soldered to the soldering points 15a, 15b in a way that is not shown, these lines connecting the coil 4 to a suitable evaluation electronics (not shown).

Moreover, the flanges 8a, 8b having the projections 9, 10, serve the purpose not only of fixing the coil sections 13a, 13b but also provide a means for fastening. In the simplest case, the motion sensor MS can have one or both flanges 8a, 8b glued to a subject to be monitored or, respectively, to a component part or the like that is rigidly connected thereto. However, there is also the possibility of fastening the motion sensor MS to a subject to be monitored or, respectively, to a component part or the like by means of screws (not shown) conducted through the oblong holes 11, 12. Finally, in a way not shown, it can also be provided that the motion sensor is contained in a housing together with evaluation electronics that is suitably attached to a subject to be monitored, for example, with a belt.

The magnet member 3 contained in the cavity 1 has the shape of a ball (diameter of approximately 2 mm) and has four magnetic poles, two north poles N and two south poles S. The position of the magnetic poles is indicated in FIG. 1 by crosses. As becomes clear from the circle shown in broken lines, the magnetic poles lie on a circular line whose center is on an axis extending through the middle M of the ball. The north poles N and the south poles S are arranged diametrically opposite one another. The arrangement is also constructed such that an angle "alpha" of 90° lies between 2 poles neighboring one another.

It is also provided in the case of the exemplary embodiment that the magnetic poles are arranged in a plane that contains the middle M of the ball with all magnetic poles having the same pole strength. As a consequence of this construction of the magnet member 3, it is in a neutral equilibrium condition in a uniform magnetic field with regards to the forces exerted on the magnetic poles by the magnetic field.

Figure 3:
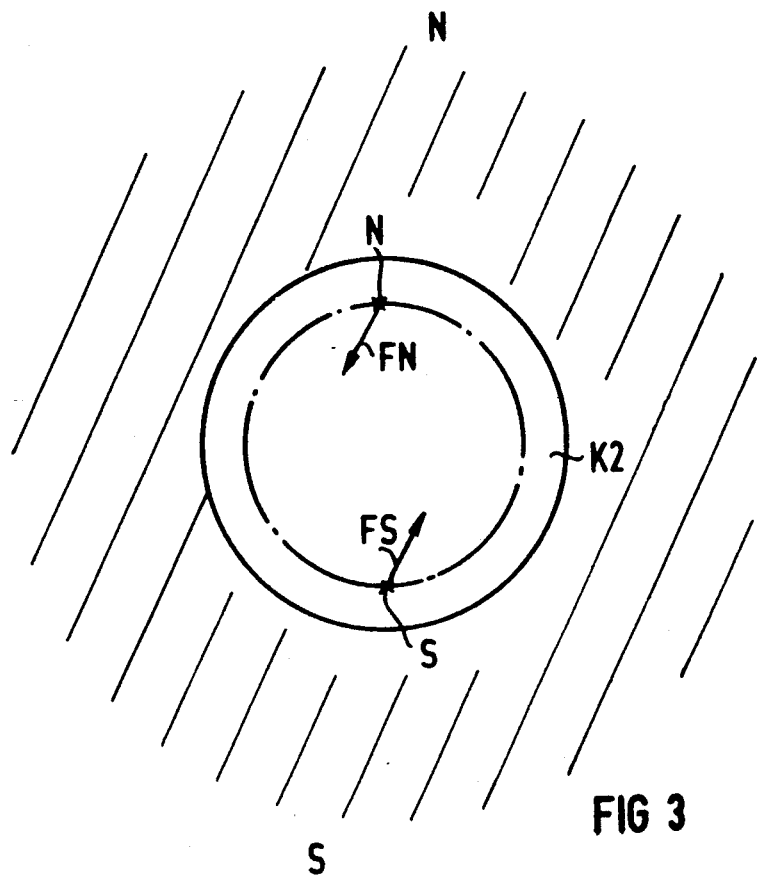
FIG. 3 is a diagram illustrating the behavior of a traditional two-pole magnet member in a uniform magnetic field.
Figure 4:
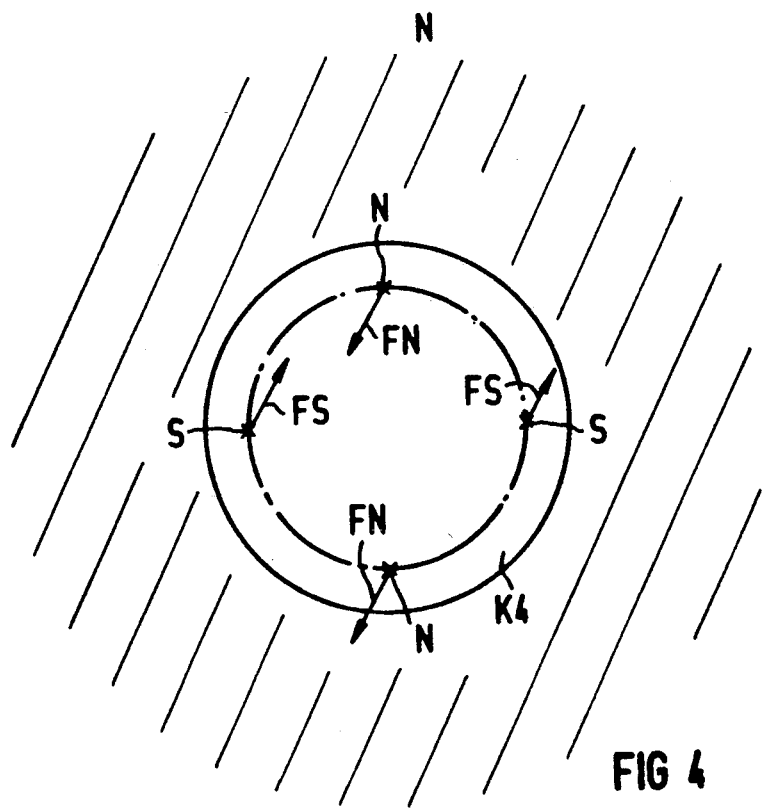
FIG. 4 is a diagram illustrating the behavior of the magnet member of the motion sensor of the present invention in a uniform magnetic field.

This becomes clear with reference to FIGS. 3 and 4. FIG. 3 shows a circular disk-shaped magnet member K2 having a north pole N and a south pole S lying diametrically opposite, this magnet member K2 being situated in a uniform magnetic field whose field lines are indicated by straight lines proceeding from north N to south S. A force FN that acts parallel to the field lines in the direction south influences the north pole N in that the north pole N strives to align toward the south. Correspondingly, a force FS that likewise proceeds parallel to the field lines but is directed toward the north influences the south pole S in that the south pole S strives to align toward the north. As a consequence of the fact that the north pole N and the south pole S that form a magnetic dipole each have respectively the same pole strength, the forces FN and FS are identical in terms of strength. Since the two forces FN and FS are directed exactly opposite one another, the sum of the forces is equal to zero.

This, however, does not apply to the position of the magnet member K2 shown in FIG. 3 with respect to the sum of the torques exerted by the forces FN and FS. Thus, under the action of the uniform magnetic field the magnet member K2 will align itself such that the north pole N points exactly toward the south and the south pole points exactly toward the north. In this situation, not only is the sum of the forces equal to zero but the sum of the torques is also equal to zero, since the force FN then has the same amount of influence as the force FS. It thus becomes clear that the magnet member K2 of FIG. 3 strives to assume a stable equilibrium position in which its north pole N points directly to the south and its south pole S points exactly to the north.

Figure 2:
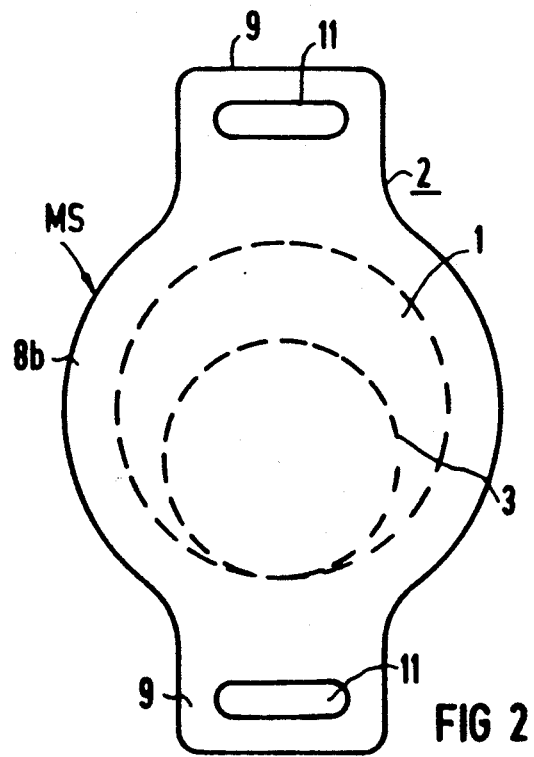
FIG. 2 is an end view of the motion sensor of FIG. 1.

When this is transferred onto a motion sensor of FIGS. 1 and 2 that, differing from the present invention, has a spherical magnet member having only two magnetic poles, namely one north pole N and one south pole S, it becomes clear that a disturbing magnetic field must produce a positional change of the magnet member, as a result whereof a current is induced in the coil 4 without the subject to which the motion sensor is attached executing any motion whatsoever. As a consequence of the fact that the magnet member K2 is situated in a stable equilibrium condition with respect to the forces exerted on the magnetic coil by a uniform magnetic field, the magnet member K2 also attenuates the magnetic field of the earth that is always present. As a result a motion sensor provided with a two-pole magnet member that otherwise corresponds to FIGS. 1 and 2 has only a comparatively low sensitivity.

FIG. 4 shows the same conditions as in FIG. 3 for a circular disc-shaped magnet member K4 that has two north poles lying diametrically opposite one another and two south poles lying diametrically opposite one another, whereby all magnetic poles have the same pole strength. The magnetic poles are arranged on a circular line in the respective spacing of 90° from one another. As in the case of FIG. 3, the sum of the forces FN and FS is equal to zero for arbitrary positions of the magnet member. By contrast to FIG. 3, it can also be easily demonstrated that the sum of the torques exerted by the forces FN and FS is also equal to zero for arbitrary positions of the magnet member K4. In the case of FIG. 4, it thus becomes clear that the magnet member K4 is situated in a neutral equilibrium condition with respect to the forces exerted on it by the uniform magnetic field. It can thereby be easily demonstrated that this is valid not only for a planar magnetic field as shown in FIG. 4 for the sake of simplicity but is also valid for a spatially uniform magnetic field, and not only for a circular disc-shaped magnet member but also for a spherical magnet member. Transferred to the motion sensor of the present invention according to FIGS. 1 and 2, this means that a uniform magnetic noise field cannot produce any motions of the spherical magnetic member 3 relative to the coil 4, so that the motion sensor of the present invention is insensitive to disturbance. As a consequence of the fact that the four-pole magnet member K4 is in a neutral equilibrium with respect to the forces exerted on the magnetic poles, a uniform magnetic field can also not attenuate the four-pole magnet member K4. It thus becomes clear that a motion sensor MS of the present invention provided with a four-pole magnet member K4 has a high sensitivity and responds to the slightest motions.

Figure 5:
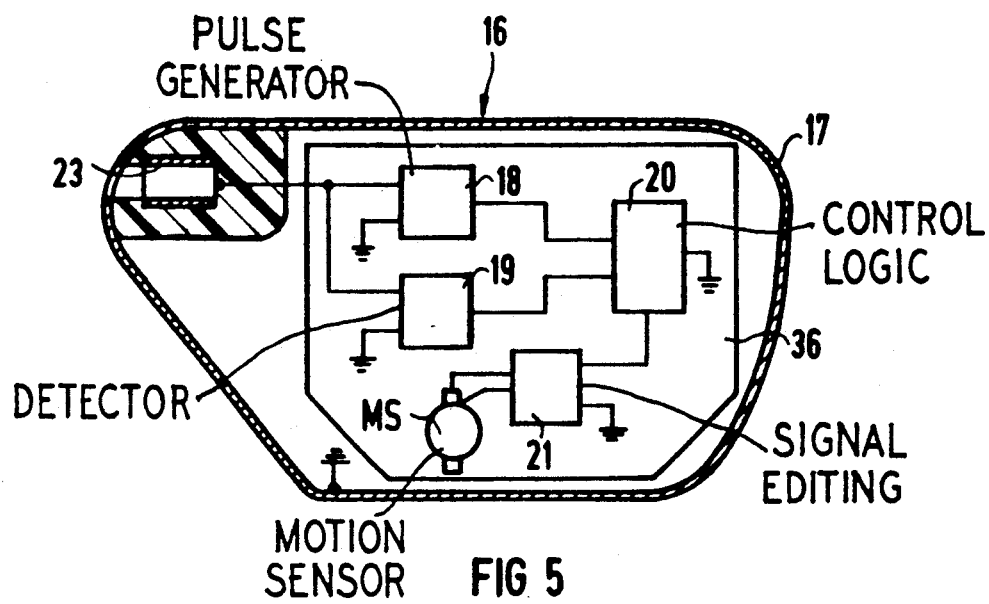
FIG. 5 is a schematic diagram of a heart pacemaker containing a motion sensor of the present invention.

FIG. 5 illustrates the use of the motion sensor MS of FIGS. 1 and 2 in a heart pacemaker 16. The heart pacemaker 16 which is provided for implantation into the body of a patient, has a hermetically tight, flat housing 17 formed of an electrically conductive material, for example titanium, this housing 17 surrounding a printed circuit 36 that carries the components of the heart pacemaker 16. The printed circuit 36 is positioned approximately parallel to the flat sides of the housing 17. The heart pacemaker 16 has a stimulation pulse generator 18 and a detector circuit 19 each of which is respectively connected to a control logic 20. The control logic 20 always initiates the stimulation pulse generator 18 to output a stimulation pulse when, following a natural heart beat detected by the detector means 19 or following a stimulation pulse output by the stimulation pulse generator 18, no natural heart beat has been detected with the detector means 19 after the expiration of a time interval corresponding to a defined heart beat frequency. The control logic 2 thereby matches the duration of the time interval corresponding to the heart beat frequency to the physical activity of the patient.

To this end, the control logic 20 is connected to a signal editing circuit 21 to which a motion sensor MS of the present invention (schematically shown in FIG. 5) is connected. The motion sensor MS is suitably secured to the printed circuit 36, for example by gluing or with a form fit. The control logic 20 sets the duration of the time interval corresponding to the heart beat frequency dependent on the signals supplied to it by the signal editing circuit 21, setting this duration between a lower limit value that corresponds to an extremely low or zero physical activity of the patient (for example, 60 beats per minute) and an upper limit value that corresponds to an extremely high physical activity of the patient (for example, 150 beats per minute). The motion sensor MS is secured to the printed circuit 36 such that the rotational axis of its cavity 1 extends essentially at a right angle relative to the plane of the printed circuit 36.

In the case of the motion sensor MS of FIGS. 1 and 2, it is also provided that the diameter of the spherical magnet member 3 is at least equal to the minimum curvature radius of the ellipsoid of revolution that forms the cavity 1. Since the heart pacemaker 16 is usually implanted in the chest region of the patient such that the flat sides of the housing 17 extend parallel to the front body side of the patient, the rotational axis of the cavity 1 extends parallel to the direction of the force of gravity when the patient is lying flat. When the patient is lying flat, the operating condition of the motion sensor MS of the present invention (shown in FIG. 6) then occurs in that the spherical magnet member 3 presses against the generated surface of the cavity 1 shaped like an ellipsoid of revolution along a circular line under the action of the force of gravity that is indicated by an arrow referenced G in FIG. 6. Thus, under the action of the force of gravity the magnet member 3 assumes an "arrested position" in which a roll-off on the wall of the cavity 1 and, thus, motions relative to the coil 4 are impossible.

Physiologically unsubstantiated increases in the stimulation frequency are impossible as a result of this measure, even under unusual sleeping conditions, for example in the sleeping car of a train, since the motion sensor MS, has the sensitivity of zero as long as the magnet member 3 is situated in the "arrested position". Only when the patient stands up again is the magnet member 3 in the position to roll freely on the wall of the cavity 1, so that a control of the stimulation frequency matched to the physical activity of the patient can occur. It can thereby be provided that the signal editing circuit 21 cooperates with the control logic 20 such that, when no signal indicating a physical activity of the patient has occurred over a longer time span, i.e. when the magnet member 3 was thus situated in an "arrested position", an especially high stimulation frequency is set for a short time span given the appearance of a signal indicating a physical activity of the patient in order to assist the patient when he assumes his physical activity.

The diameter of the spherical magnet member 3 need not necessarily be larger than the minimum curvature radius of the cavity 1, this being the prerequisite for completely suppressing a roll-off of the magnet member 3 on the wall of the cavity 1. On the contrary, it can even be adequate in certain instances when the diameter of the magnet member 3 approximately reaches the minimum curvature radius of the cavity 1. In this case, a free roll-off of the magnet member 3 on the wall of the cavity 1 is in fact not completely suppressed when the rotational axis of the cavity 1 is aligned parallel to the direction of the force of gravity. It is, however, greatly inhibited, which leads to a greatly reduced sensitivity of the motion sensor.

The stimulation pulse generator 18 also has an output carrying the stimulation potential and an output carrying a reference potential, whereby the latter is identified by a ground symbol. In corresponding fashion, the detector means 19 has an input for receiving the potential corresponding to the electrical activity of the heart to be stimulated and has a terminal that receives a reference potential, whereby the latter is again identified by the ground symbol. Both the output of the stimulation pulse generator 18 carrying the stimulation potential as well as the input of the detector means 19 are connected to a connector jack 23 to which a unipolar, endocardial electrode (not shown) can be connected, this electrode being conducted through the vein system of the patient to his heart. The electrode first serves the purpose of charging the heart of the patient with the stimulation pulses generated with the stimulation pulse generator 18 and, second, serves the purpose of supplying the signal that corresponds to the electrical activity of the heart to the detector means 19. The reference potential is applied via the housing 17 of the heart pacemaker 16 to the tissue of the patient that surrounds the heart pacemaker 16, this being indicated in that the housing 17 is provided with a ground symbol.

As a consequence of the fact that the motion sensor 22 of the present invention can not be disturbed by the magnetic field of the earth or by low-frequency magnetic fields emanating from electrical devices, even slight physical activities are reliably detected, so that the heart pacemaker 17 provided with the motion sensor MS of the present invention is particularly suitable for older patients. Added thereto as a further advantage is that a physiologically unsubstantiated rise of the stimulation frequency is practically impossible when the patient is lying down since a roll-off of the spherical magnet member 3 on the wall of the cavity 1 is impossible when the patient is in this position.

Figure 7:
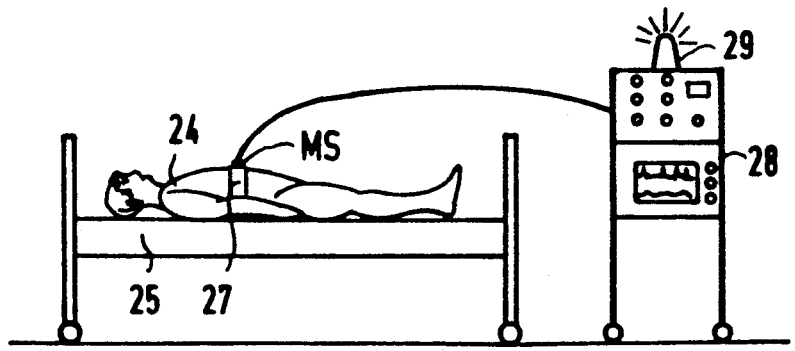
FIG. 7 depicts the use of the motion sensor of the present invention for monitoring a bed-ridden patient.

For the same reasons that the motion sensor of the present invention is used in heart pacemakers, it is also especially suited for monitoring bed-ridden patients. This is illustrated in FIG. 7 with reference to the example of a patient 24 in need of intensive care, for example, a patient that has been anesthetized or is in a coma. The patient 24 lies in a bed 25 and is provided with a box containing a motion sensor MS of the present invention, this box being secured to the patient's chest with a belt 27. The motion sensor MS contained in the box is in communication via a line with a monitoring means 28 that has a light signal 29 that is activated a soon as the physical activity of the patient 24 exceeds a specific, adjustable level. The monitoring means 28 also serves the purpose of monitoring further physiological functions of the patient such as, for example, his cardiac and respiratory activity.

Figure 8:
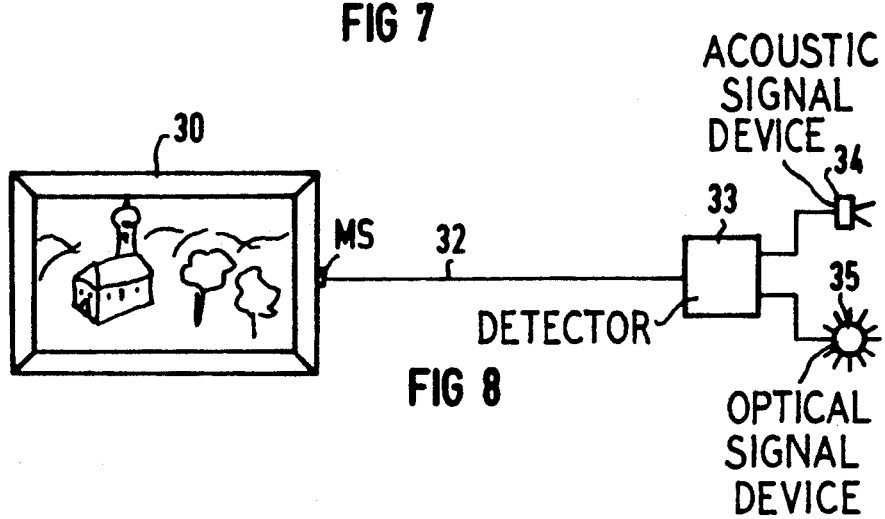
FIG. 8 depicts the use of the motion sensor of the present invention as an anti-theft sensor.

The use of the motion sensor MS of the present invention as an anti-theft sensor is shown in FIG. 8. This schematically shows a painting 30 to whose frame a motion sensor MS of the present invention is attached, the motion sensor MS being connected via a line to a detector circuit 33. As soon as the painting 30 is moved or, respectively, as soon as the line 32 is parted, the detector circuit activates an acoustic signal means 34 and/or an optical signal means 35. As a consequence of the described properties of the motion sensor MS of the present invention and by contrast to known inductive motion sensors, it cannot be disabled by a thief by simply using a permanent magnet.

Given both motion sensors MS provided for monitoring bed-ridden patients as well as for anti-theft security, it will usually be appropriate to fashion the cavity 1 thereof spherically, so that an identically great sensitivity of the motion sensor MS is guaranteed for arbitrary attitudes of the subject to be monitored. It can also be expedient to fashion the cavity 1 spherically for motion sensors MS used in heart pacemakers, for example when additional sensors can be used to determine whether the patient is in the condition of rest, for example, in a lying position.

A further exemplary embodiment of a motion sensor of the invention particularly provided for use in a heart pacemaker is shown in FIG. 9. This differs only slightly from the exemplary embodiments set forth above, so that the respectively same reference characters are employed for respectively identical parts, being provided with a ' in the case of FIG. 9. A first difference of the motion sensor MS' compared to that set forth above is that the housing 2' surrounds a cavity 1' having the approximately shape of a lemon that is rotationally symmetrical relative to the rotational axis identified with broken lines in FIG. 9. In the case of the motion sensor MS' the magnet member 3' that preferably corresponds to that of the exemplary embodiment set forth above assumes an "arrested position" in which a roll-off on the wall of the cavity 1' is impossible when the rotational axis of the cavity 1' extends essentially parallel to the direction of the force of gravity. The lemon-shaped form of the cavity 1' thereby offers the advantage that the magnet member 3', given the described alignment of the motion sensor M' relative to the direction of the force of gravity, is completely inhibited from rolling-off on the wall of the cavity 1' regardless of the size of its diameter.

A further difference of the motion sensor MS' compared to that set forth above is a somewhat different shaping of the housing 2'. This is provided so that it can be mounted in the bore 37 of a printed circuit 36'. The flanges 8a' and 8b' of the housing parts 5a' and 5b' are therefore executed in the shape of a circular disc without any projections whatsoever. Instead, the housing part 5b' is provided with a collar 38 in the region of its end neighboring the flange 8b', this collar 38 lying to the side at the one side of the printed circuit 36' when the motion sensor MS' is mounted. In the region of its free end, the centering edge 7' is provided with a plurality of elastically resilient clips 39 that deform radially inwardly upon introduction of the motion sensor MS' into the bore 37 but spring back radially outwardly when the motion sensor MS' is completely introduced into the bore 37 and thus affect a play-free holding of the motion sensor MS' in the bore 37. It becomes clear with reference to FIG. 5 that these measures guarantee that the incorporation of the motion sensor MS' in a heart pacemaker guarantees that the magnet member 3' is situated in an "arrested position" when the patient lies flat.

The ends 40a, 41a or, respectively, 40b, 41b of the coil sections 13a' and 13b' of the coil 4' are directly soldered (in a way not shown) to the solder points of the printed circuit 36' which are provided for this purpose.

In the case of the exemplary embodiment of FIGS. 1, 2 and 6, the magnet member 3 has respectively two south poles and two north poles. Within the scope of the present invention, however, the magnet member 3 can also have a greater plurality of magnetic poles, insofar as it is merely guaranteed that the number of south poles is identical to the number of north poles. It is also provided in the case of the described exemplary embodiment that all magnet poles have the same pole strength, are arranged on a circular line and have the respectively same angular spacing relative to one another. Within the scope of the present invention, however, a different arrangement can also be undertaken insofar as it is merely assured that the pole strength of the magnetic poles is dimensioned such and the magnetic poles are placed such at the magnet member that this magnet member is in a neutral equilibrium position in a uniform magnetic field.

The magnet member is preferably composed of a magnetizable material, for example an iron alloy, and is properly magnetized. The magnet member, however, can also be composed of a non-magnetizable material, for example, a polymeric material, into which magnets are suitably introduced.

When, given motion sensors whose cavity is shaped such that the roll-off of the magnet member is impeded or completely suppressed given a specific alignment of the motion sensor, overriding priorities accorded less to a high reliability against disturbance than to a positionally highly dependent function of the motion sensor, magnet members can also be used that are traditionally fashioned, i.e. assume a stable equilibrium position in a uniform magnetic field. For example, such a motion sensor could be used in a heart pacemaker in order to be able to detect whether the patient assumes a lying position. The actual control of the stimulation frequency dependent on the physical activity of the patient would then have to occur with a further, suitable sensor whose signal is only taken into consideration when the patient is not in lying position.

The invention is not limited to the particular details of the apparatus depicted and other modifications and applications are contemplated. Certain other changes may be made in the above described apparatus without departing from the true spirit and scope of the invention herein involved. It is intended, therefore, that the subject matter in the above depiction shall be interpreted as illustrative and not in a limiting sense.

What is claimed is:

1. Inductive motion sensor connected to a subject, the inductive motion sensor having a coil and a magnet member movable relative to said coil, comprising: said magnet member being in a region free of magnetic materials having at least four magnetic poles, the number, of south poles being identical to the number of north poles; and the pole strength of the magnetic poles being dimensioned and the magnetic poles being located on the magnet member such that the magnet member is situated in a neutral equilibrium position with respect to external forces exerted on the magnetic poles by a uniform magnetic field, whereby said motion sensor senses movement of the subject by means of a dislocation of said magnetic member relative to said coil.

2. Motion sensor according to claim 1, wherein said motion sensor comprises a housing surrounding a cavity, said magnet member contained in said cavity; and wherein said housing is substantially surrounded by said coil.

3. Motion sensor according to claim 2, wherein said coil is wound onto the outside of said housing.

4. Motion sensor according to claim 2, wherein sad spherical magnet member rolls-off on a wall of said cavity.

5. Motion sensor according to claim 2, wherein said cavity is substantially rotationally symmetrical.

6. Motion sensor according to claim 5, wherein said cavity is shaped such that said motion sensor has at least one alignment for which a roll-off of said magnet member relative to the direction of the force of gravity on a wall of said cavity is impeded.

7. Motion sensor according to claim 5, wherein said cavity at least approximately has the shape of an ellipsoid of revolution.

8. Motion sensor according to claim 5, wherein said cavity has a substantially lemon-shaped configuration.

9. Motion sensor according to claim 1, wherein said magnetic poles each respectively have substantially the same pole strength and are arranged at substantially identical angular spacings from one another on a substantial circular line such that a north pole is respectively followed by a south pole.

10. Motion sensor according to claim 1, wherein said magnet member has a substantially spherical configuration.

11. Motion sensor according to claim 1, wherein the subject is a life form and the motion sensor is located in a heart pacemaker of the life form, a stimulation frequency of the motion sensor controlled as a function of physical activity of the life form having the heart pacemaker.

12. Motion sensor according to claim 1, wherein the subject is a bed-ridden patient and the motion sensor monitors the bed-ridden patient.

13. Motion sensor according to claim 1, wherein the subject is an object and the motion sensor is an anti-theft sensor.

* * * * *